United States Patent
Sugamura et al.

(10) Patent No.: US 6,333,035 B1
(45) Date of Patent: Dec. 25, 2001

(54) MEDICINAL COMPOSITION CONTAINING GP34 BINDING-INHIBITOR AS THE ACTIVE INGREDIENT

(75) Inventors: Kazuo Sugamura; Kazuko Murata, both of Sendai; Norikazu Higashimura, Mobara, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/308,332

(22) PCT Filed: Sep. 24, 1998

(86) PCT No.: PCT/JP98/04282

§ 371 Date: May 19, 1999

§ 102(e) Date: May 19, 1999

(87) PCT Pub. No.: WO99/15200

PCT Pub. Date: Apr. 1, 1999

(30) Foreign Application Priority Data

Sep. 25, 1997 (JP) ..................................... 9-260278
Sep. 21, 1998 (JP) .................................. 10-266452

(51) Int. Cl.[7] ................................. A61K 39/395

(52) U.S. Cl. ................................... 424/144.1; 424/130.1; 424/133.1; 424/174.1; 424/184.1; 530/388.22

(58) Field of Search .............................. 424/130.1, 133.1, 424/144.1, 184.1, 174.1; 530/388.22

(56) References Cited

FOREIGN PATENT DOCUMENTS

| WO95/05468 | 2/1995 | (WO) . |
| WO95/21251 | 8/1995 | (WO) . |
| WO95/21915 | 8/1995 | (WO) . |

OTHER PUBLICATIONS

Slaviadis, T et al. et al., PNAS 83:6146–50, 1986.*
Waldman, T.A. et al., Science 252:1657–1662, 1991.*
Dijikstra, C. et al, TiPS, 14:124–129, 1993.*
Imura et al, "The Human OX40/gp34 System Directly Mediates Adhesion of Activated T Cells to Vascular Edothelial Cells", J. Exp. Med., 1996, vol. 183, No. 5, 2185–2195.
Tanaka et al, A Glycoprotein Antigen Detected with New Monoclonal Antibodies on the Surface of Human Lymphocytes Infected with Human T–Cell Leukemia Virus Type–I (HTLV–I), Int. J. Cancer, 36, 549–555, 1985.
Miura et al, Molecular Cloning and Characterization of a Novel Glycoprotein, gp34, That is Specifically Induced by the Human T–Cell Leukemia Virus Type I Transactivator $p40^{tax}$ Mol. Cell. Biol., 11, 1313–1325, 1991.
Paterson et al, "Antigens of Activated Rat T Lymphocytes Including a Molecule of 50,000 $M_r$., Detected Only on CD4 Positive T Blasts", Mol. Immunol. 24, 1281–1290, 1987.
Godfrey et al, Identification of a Human OX–40 Ligand, a Costimulator of CD4[+] T Cells with Homology to Tumor Necrosis Factor, J. Exp. Med., 180, 757–762, 1994.
Baum et al., "Molecular Characterization of Murine and Human OX40/OX40 Ligand Systems: Identification of a Human OX40 Ligand as the HTLV–1–Regulated Protein gp34", EMBO J. 13, 17, 3992–4001, 1994.

(List continued on next page.)

Primary Examiner—David Saunders
Assistant Examiner—Amy DeCloux
(74) Attorney, Agent, or Firm—Burns, Doane, Swecker & Mathis, L.L.P.

(57) ABSTRACT

The present invention relates to a pharmaceutical composition for the therapeutic treatment of autoimmune diseases including rheumatoid arthritis, multiple sclerosis, sarcoidosis, autoimmune uveitis, and inflammatory bowel disease, or graft-versus-host disease. The pharmaceutical composition contains, as the effective ingredient, a gp34 binding-inhibitory substance.

2 Claims, 4 Drawing Sheets

BINDING OF shOX40-Fc TO MOUSE gp34-EXPRESSING CELL

OTHER PUBLICATIONS

Weinberg et al, "Selective Depletion of Myelin–Reactive T Cells with the Anti–OX–40 Antibody Ameliorates Autoimmune Encephalomyelitis", Nature Med., 2, 2, 183–189, 1996.

Karasuyama et al, "The Proteins Encoded by the $V_{preB}$ and $\lambda_5$ Pre–B Cell–Specific Genes Can Associate with Each Other and with $\mu$ Heavy Chain", J. Expo. Med., 172, 969–972, 1990.

Tateno et al, "Rat Lymphoid Cell Lines with Human T–Cell Leukemia Virus Production", J. Exp. Med., 159, 1105–1116, 1984.

Schulman et al, "A Better Cell Line for Making Hybridomas Secreting Specific Antibodies", Nature, 276, 269–270, 1978.

Kondo et al, "Sharing of the Interleukin–2 (IL–2) Receptor $\lambda$ Chain Between Receptors for IL–2 and IL–4", Science, 262, 1874–1877, 1993.

* cited by examiner

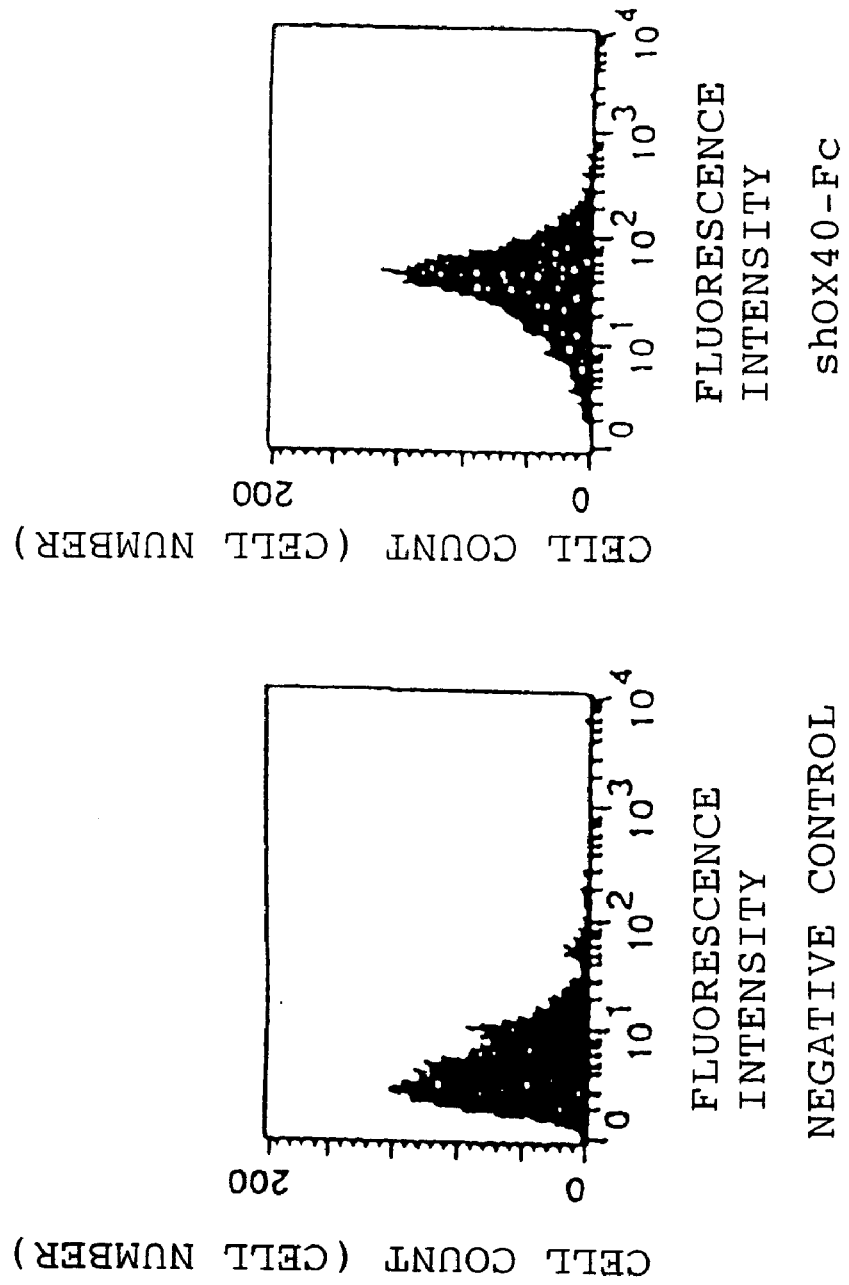
FIG. 1 BINDING OF shOX40-Fc TO MOUSE gp34-EXPRESSING CELL

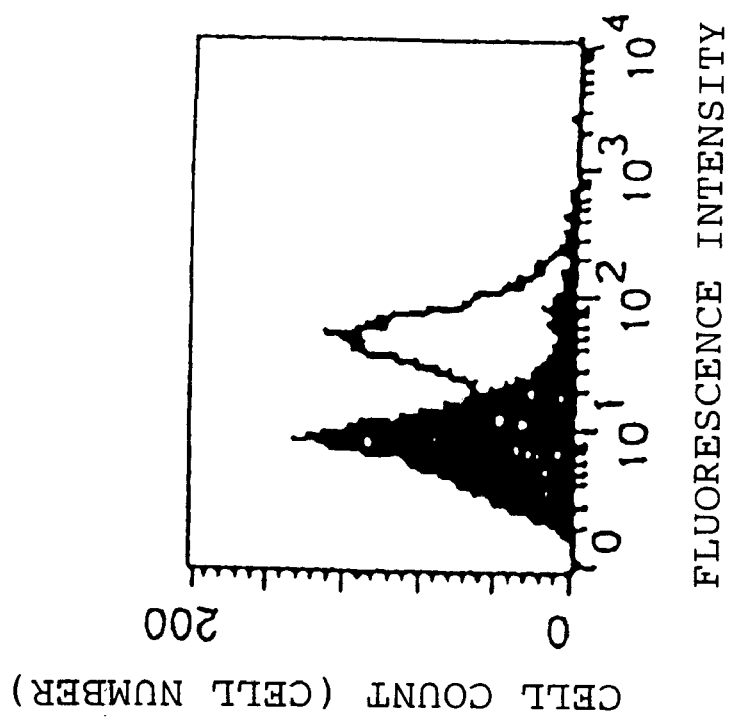
FIG. 2 INHIBITION OF RAT ANTI-MOUSE gp34 MONOCLONAL ANTIBODY OVER BINDING BETWEEN MOUSE gp34 AND shOX40-Fc

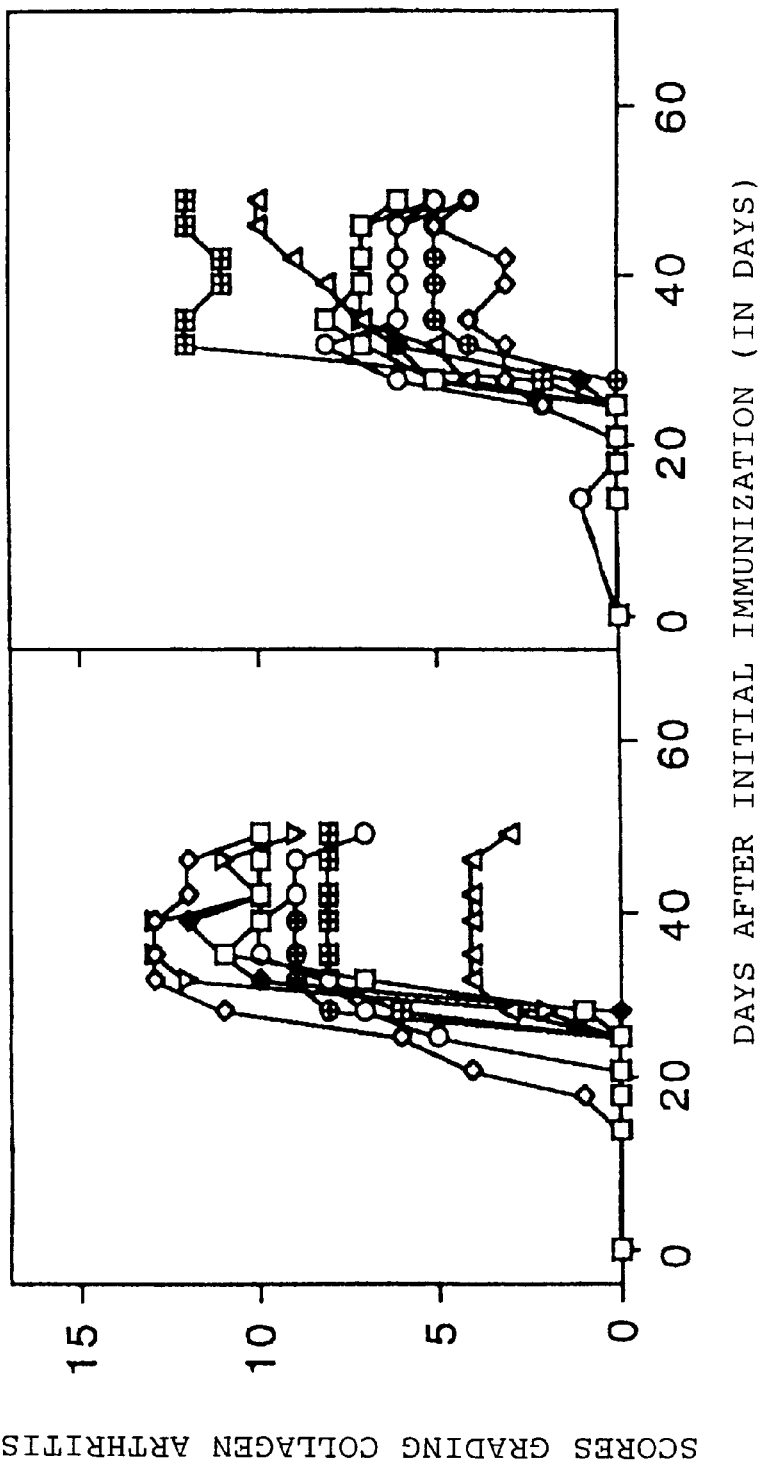
FIG. 3  EFFECT OF RAT ANTI-MOUSE gp34 MONOCLONAL ANTIBODY OVER COLLAGEN ARTHRITIS

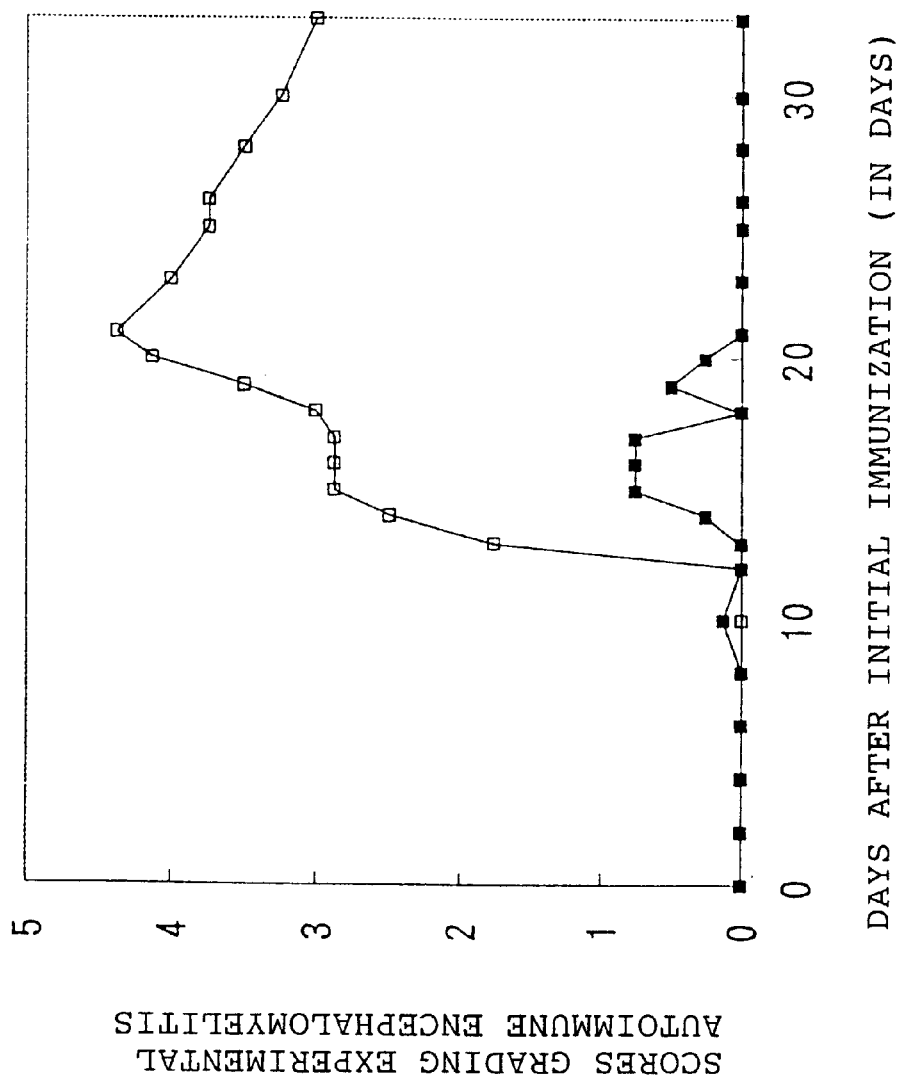
FIG. 4 EFFECT OF RAT ANTI-MOUSE gp34 MONOCLONAL ANTIBODY OVER EXPERIMENTAL AUTOIMMUNE ENCEPHALOMYELITIS

MEDICINAL COMPOSITION CONTAINING GP34 BINDING-INHIBITOR AS THE ACTIVE INGREDIENT

This application is a national stage filing under 35 USC 371 from PCT/JP98/04282, filed Sep. 24, 1998.

TECHNICAL FIELD

The present invention relates to a pharmaceutical composition for the therapeutic treatment of immune cell-mediated diseases, specifically a pharmaceutical composition containing as the effective ingredient a substance binding to gp34 antigen and having inhibitory potency of the biological activity between the membrane proteins of antigens gp34 and OX40. More specifically, the invention relates to a novel pharmaceutical composition being responsible for the cellular signal transduction mechanism via gp34 and having a therapeutic action over autoimmune diseases including rheumatoid arthritis, multiple sclerosis, sarcoidosis, autoimmune uveitis and inflammatory bowel disease, and graft-versus-host disease.

BACKGROUND OF THE INVENTION

Human gp34 antigen belongs to a ligand family of tumor necrosis factor (referred to as "TNF" hereinbelow) classified as cytokine. Firstly, the gp34 antigen was identified as a human T-cell leukemia virus (referred to as HTLV-1 hereinbelow)-derived transcription activating factor p40Tax induced T-cell membrane glycoprotein of 34 kDa. Currently, the amino acid sequence of the gp34 antigen and DNA nucleotide sequence of the gene thereof are known (Tanaka et al: Int. J. Cancer 36, 549 (1985), Miura et al.: Mol. Cell. Biol. 11, 1313 (1991)). Meanwhile, the OX40 antigen has been identified as an activated T-cell antigen in rats (Paterson et al.: Mol. Immunol. 24, 1281 (1987)). Thereafter, it has been revealed that the gp34 antigen has a ligand-receptor relation with the OX40 antigen in humans and mice. The amino acid sequence of murine gp34 and the DNA nucleotide sequence of the gene thereof have been known (Godfrey et al.: J. Exp. Med. 180, 757 (1994), Baum et al.: EMBO J.13, 3992 (1994)). Furthermore, it has been elucidated at experimental autoimmune encephalomyelitis (referred to as "EAE" hereinafter)in rats that such OX40 antigen is expressed in an activated CD4-positive T-cell being contained in autoimmune diseases including multiple sclerosis, rheumatoid arthritis, sarcoidosis, autoimmune ocular diseases and inflammatory bowel disease and in graft-versus-host disease and functioning as autoimmunity, and that the specific elimination of the self-attacking CD4-positive T cells at an activated state by binding a cytotoxin to a substance recognizing such OX40 antigen may be promising as an effective therapeutic method. A patent application has been submitted therefor, while a report has also been issued (CANTAB PHARM, Res., Lim.: WO95/21251, Weinberg et al: Nature Med. 2, 183 (1996)). The report describes that a group of OX40-positive cells is present in activated CD4-positive T cells with self-reactivity among CD4-positive activated cells and an anti-OX40 immunotherapy against them may be effective as the therapeutic treatment of acute or chronic autoimmune diseases mediated via CD4-positive T cells. However, the report tells that the expression of OX40 is just a simple marker of cells responsible for autoimmune diseases and the therapeutic effect is owing to the elimination of target activated T cells. The report additionally tells that it is not yet elucidated whether or not such inflammatory state or autoimmune state can be suppressed by singly blocking the binding between gp34 and OX40 and that single addition of anti-OX antibody with no cytotoxin bound thereto did not suppress the cell growth of activated CD4-positive T lymphocytes responsible for the exacerbation of the symptomatic conditions. It is also reported that a rabbit anti-mouse OX40 polyclonal antibody bound with a cytotoxin suppressed the elevation of the score grading the symptomatic conditions in EAE, but no such effect is reported in a concurrently examined group dosed with only a rabbit anti-mouse OX40 polyclonal antibody or in a negative control alike. The finding indicates that it is not yet elucidated whether the inhibition of only the binding between gp34 and OX40 can suppress the inflammatory state or autoimmune state. Additionally, a patent application has been submitted, regarding a method for detecting inflammatory symptoms of a patient with a disease believed to be mediated with activated T lymphocytes, comprising examining an biopsy sample from the patient (CANTAB PHARM, Res, lim.: WO95/21251).

As has been described above, the functions of gp34 and OX 40 have been elucidated just partially. The relation between gp34 and OX40 and the role thereof in various autoimmune diseases have absolutely never been elucidated so far. Specific inhibition of the function mediated between these two molecules on the side of gp34 by using an anti-human gp34 monoclonal antibody has totally never been anticipated. In other words, it has never been known whether or not such inhibition is effective for the therapeutic treatment of autoimmune diseases including rheumatoid arthritis, multiple sclerosis, sarcoidosis, autoimmune uveitis and inflammatory bowel disease, and graft-versus-host disease.

Problems that the Invention is to Solve

It is an object of the invention to provide a novel pharmaceutical composition containing as the effective ingredient a human gp34 binding-inhibitory substance, more specifically a humanized anti-human gp34 monoclonal antibody, as a therapeutic agent for autoimmune disease including rheumatoid diseases including multiple sclerosis, sarcoidosis, autoimmune uveitis or inflammatory bowel disease, or graft-versus-host disease; and a method for therapeutically treating immune- or autoimmune diseases, comprising inhibiting binding to gp34, particularly binding to OX40.

Means for Solving the Problems

So as to overcome the problems, the inventors have made investigations. Consequently, the inventors have recovered a rat anti-mouse gp34 monoclonal antibody believed to have the same properties as those of a humanized monoclonal antibody binding to human gp34. Because gp34 experiments in patients with rheumatoid arthritis and multiple sclerosis cannot be practiced, ethically, the recovered rat anti-mouse gp34 monoclonal antibody was given to a collagen arthritis-triggered model mouse and an experimental autoimmune encephalomyelitis-triggered model mouse, whereby it was confirmed that the onset of the symptomatic conditions was suppressed in the rheumatoid model and the multiple sclerosis model. The finding firstly reveals that the binding between OX40 and gp34 on an OX40-positive activated T cell triggers autoimmune diseases such as rheumatism. The finding is indicated at the mouse experiments, but it is possibly suggested that the effect in mouse should also be exerted in humans because the properties of mouse gp34 and mouse OX40 are common to the properties of human gp34 and human OX40 in such a manner that gp34 and OX40 are in a relation between ligand and receptor. More specifically, the finding unconditionally indicates that a monoclonal antibody with binding potency to human gp34 is effective as a therapeutic agent for autoimmune diseases including rheumatoid arthritis, multiple sclerosis, sarcoidosis, autoimmune uveitis and inflammatory bowel disease, and graft-versus-host disease.

In other words, the present invention is a pharmaceutical composition containing as the effective ingredient a gp34 binding-inhibitory substance for the therapeutic treatment of autoimmune diseases, or a pharmaceutical composition containing as the effective ingredient a gp34 binding-inhibitory substance for the therapeutic treatment of immune diseases.

BRIEF DESCRIPTION OF THE DRAWINGS

FIG. 1 depicts graphs expressing the binding specificity of shOX40-Fc to mouse gp34-expressing cell.

FIG. 2 is a graph expressing the inhibition of rat anti-mouse gp34 monoclonal antibody over the binding between mouse gp34 and shOX40-Fc. Open zone represents the fluorescence intensity prior to the addition of the rat anti-mouse gp34 monoclonal antibody; closed zone represents the fluorescence intensity after the addition of the rat anti-mouse gp34 monoclonal antibody.

FIG. 3 depicts graphs expressing the efficacy of the rat anti-mouse gp34 monoclonal antibody over the inhibition of the onset of bovine type 2 collagen arthritis; the change of the scores grading arthritis in individual samples after the induction of collagen arthritis is plotted with time; in the figure, each symbol represents each animal.

FIG. 4 depicts graphs expressing the efficacy of the rat anti-mouse gp34 monoclonal antibody over the inhibition of the onset of experimental autoimmune encephalomyelitis; the change of the mean of the scores grading experimental autoimmune encephalomyelitis in individual samples after the induction of experimental autoimmune encephalomyelitis is plotted with time; in the figure, open part represents a group dosed with the rat anti-mouse gp34 monoclonal antibody; and closed part represents a group dosed with rat immunoglobulin G.

MODE OF CARRYING OUT THE INVENTION

The term "gp34 binding-inhibitory substance" means a substance with a function to inhibit the binding to gp34 and thereby inhibit the cellular signal tranduction between ligand and receptor, particularly a substance functioning on the side of gp34 for the inhibition of such binding. As those binding to gp34, OX40 is a particularly representative one. The gp34 binding-inhibitory substance includes for example a specific antibody against gp34, specifically a monoclonal antibody against gp34. The monoclonal antibody in accordance with the invention can be recovered by replacing the antigen binding site of an anti-human gp34 monoclonal antibody prepared from other animals, including the rat monoclonal antibody, with the constant region of a human antibody and then preparing a chimera antibody or a humanized antibody by using various known methods.

The amino acid sequences of human- and mouse gp34's and the DNA nucleotide sequences of the genes thereof have been known. Therefore, cells generating monoclonal antibodies against them, particularly hybridomas, may be prepared by generally known methods, and an anti-gp34 monoclonal antibody may be generated by using the cells.

The generation of the monoclonal antibody in accordance with the invention may successfully be attained, by culturing a cell strain generating the humanized anti-human gp34 antibody by using various known methods and purifying the recovered crude antibody. Any method with no inhibition over cell growth and over the generation of the humanized anti-human gp34 monoclonal antibody may be satisfactory, with no specific limitation. The composition of the invention contains gp34 binding-inhibitory substances such as gp34 monoclonal antibody as the effective ingredient, and may additionally contain pharmaceutically acceptable additives.

The pharmaceutical composition of the invention is administered to patients with immune diseases such as graft-versus-host disease and autoimmune diseases such as rheumatoid arthritis, multiple sclerosis, sarcoidosis, autoimmune uveitis and inflammatory bowel disease.

EXAMPLES

The invention will now be described in examples, but the invention is not limited to them.

Example 1
Preparation of Rat Anti-mouse gp34 Monoclonal Antibody
a. Immunization with Mouse gp34

By using a reverse transcriptase, mouse gp34 gene was cloned from RNA extracted from murine splenocytes stimulated with ConA (Baum et al.: EMBO J. 13, pp.399 z-4001, (1994)). The mouse gp 34 gene fragment was inserted into a plasmid BCMGSNeo (Karasuyama et al.: J. Exp. Med. 172, 969, (1990)) to be then prepared as BCMGSNeo-mgp34 plasmid. The gene carried on the plasmid was then inserted into a WKA/Hoc rat T-cell strain TART-1 (Tateno et al.: J. Exp. Med. 159, 1105(1984)) by electroporation. Subsequently, a resistant cell strain was selected on the basis of neomycin resistance. The expression of the mouse gp34 gene was verified by using the RNA extracted from the selected cell strain by RT-PCR, to recover a mouse gp34-expressing cell strain TART-mgp34. The mouse gp34-expressing cell strain TART-mgp34 was inoculated at $1 \times 10^8$ cells, every two weeks, seven times, into the posterior limb flesh hummock part of a Wister rat of age 8 weeks (manufactured by Nippon SLC, CO.). Three days after the final immunization, the spleen was then resected from the rat. The resected splenocyte was rinsed three times in an RPMI-1640 culture medium (manufactured by Nissui Pharmaceuticals, Co.). Meanwhile, a mouse myeloma cell strain SP2/0-Ag14 (Schulman et al.: Nature 276, 269 (1978)) was grown to a logarithmic growth phase and then rinsed three times in an RPMI-1640 culture medium. The mouse myeloma cell strain SP2/0-Ag14 was blended with the splenocyte at a ratio of 1:3, and the resulting mixture was centrifuged at 1,000 rpm for 10 minutes to discard the supernatant. To the precipitated cells was slowly added 1 ml of an RPMI-1640 culture medium kept warm at 37° C., under mild agitation, over one minute. One milliliter of an RPMI-1640 culture medium kept warm at 37° C. was again added slowly under mild agitation over one minute. Additionally, 1 ml of a 50% polyethylene glycol 4000 (manufactured by Merck & Co., Inc.) solution kept warm at 37° C. was added over 1 minute under mild agitation, and the resulting mixture was slowly agitated for another one minute. Additionally, 7 ml of an RPMI-1640 culture medium kept warm at 37° C. was added under mild agitation over three minutes. At ambient temperature, the mixture was centrifuged at 1,000 rpm for 5 minutes, to discard the supernatant. An RPMI-1640 culture medium containing 10% fetal calf serum (referred to as "FCS" hereinafter) and having been kept warm at 37° C. was added to the resulting cells to a final cell concentration of $5 \times 10^6$ cells/ml, to suspend the cells under gentle agitation. The suspended cells were divided in 50-μl portions at each portion per one well of a 96-well culture plate, for overnight culturing in a cell incubator. On the day next, 100 µl each of a HAT medium (RPMI-1640 culture medium containing 0.1 mM hypoxanthine, 0.4 µM aminopterin, 16 µM thymidine, and 15% FCS) was added to each well. Under observation of the growth state of the cells, subsequently, 100 µl each of the culture medium was exchanged to a fresh HAT medium. During such procedures, growing fused cells were prepared as hybridoma.

b. Confirmation of Antibody Generation

The hybridoma generated above in a. was cultured, and 12 days after the initiation of culturing, the whole culture supernatant was recovered. The antibody activity in the supernatant was assayed by radioimmunoassay (referred to as "RIA" hereinbelow), by using a mouse T cell-derived cell strain BW5147-mgp34 expressed via the insertion of mouse gp34 gene and the parent cell strain BW5147 (Kondo et al.: SCIENCE 262, 1874 (1993)) derived from mouse T cell, as an antigen-expressing cell and a negative control cell thereof, respectively. BW5147-mgp34 and BW5147 were cultured, rinsed in phosphate buffer (PBS(−)) and inoculated at 1×10$^6$ cells per well in a 96-well U-bottom plate. 40 µl of the supernatant of the hybridoma culture was added and blended to the cells. The 96-well U-bottom plate was kept cold on ice for 30 minutes for sufficient reaction with the antigen. The cells were rinsed twice in cold PBS (−) preliminarily kept cold at 4° C. The cells were centrifuged and prepared as a pellet, to which was added 30 µl of a sheep anti-mouse immunoglobulin G antibody labeled with a radioactive iodide I$^{125}$ (manufactured by Amersham). Then, the mixture was subjected to the reaction for 30 minutes on ice. The cells were then rinsed thrice in cold PBS (−) preliminarily kept cold at 4° C. The cells were dried by using a dryer at 90° C. for 10 minutes, to evaporate water therefrom. Subsequently, individual wells were cut out of the 96-well U-bottom plate with a pair of scissors and subjected to assaying with a gamma counter (ARC600; manufactured by Aloka). When value detected with the gamma counter was 1,000 or more in the case using the BW5147-mgp34 cell and about 50 in the case using the BW5147 cell, a well containing the hybridoma culture supernatant showing a difference of this extent between both was defined as positive cell. The reproducibility was confirmed. Cells with confirmed antibody activity were subjected to cloning by limited dilution. As a result, a rat anti-mouse gp34 monoclonal antibody-generating hybridoma strain was recovered. The hybridoma strain was designated as TOL-1, and was then deposited under FERM BP-6509 in National Institute of Bioscience and Human-Technology, Agency of Industrial Science and Technology.

c. Antibody Preparation

Twice on days 1 and 7, 0.5 ml of pristane (2,6,10,14-tetramethylpentadecane) was intraperitoneally injected into a BALB/c-nu nude mouse (manufactured by Nippon SLC). Three days after the second injection, the hybridoma strain TOL-1 (FERM BP-6509) cultured in an RPMI-1640 culture medium containing 20% FCS was intraperitoneally boosted at 10$^8$ cells per one animal. Two week later, then, the abdominal fluid was recovered. To the recovered abdominal fluid was added sodium azide to a final concentration of 0.02%, and the mixture was left to stand overnight at ambient temperature. On the day next, the abdominal fluid left to stand was centrifuged at 3,000 rpm at 4° C. for 20 minutes, to recover the supernatant. The culture supernatant was passed through a membrane of a diameter of 0.45 µm, and applied to a Protein A column kit (manufactured by BioRad Co.) to recover an immunoglobulin fraction. The recovered solution was subjected to fractionation with 50% saturated ammonium sulfate (manufactured by Wako Pure Chemical Industries, Co.), followed by re-dissolution in PBS (−) at the physiological concentration. The resulting solution was dialyzed against PBS (−), filtered through a 0.2-µm filter for aseptic treatment and subjected to use.

Example 2

Verification of Binding of Rat Anti-mouse gp34 Monoclonal Antibody to Mouse gp34 Antigen by Flow Cytometer Analysis By using the fused protein between the extracellular region of a human OX40 binding to mouse gp34 antigen and the human immunoglobulin Fc region (the protein is referred to as "shOX40-Fc" hereinbelow; supplied by Immunex, CO., USA), the binding thereof to the BW5147-mgp34 cell expressing mouse gp34 antigen was examined. 1×10$^6$ cells were recovered in a 1.5-ml tube and were centrifuged at 5,000 rpm for 30 seconds, to precipitate the cells. To the precipitated cells was added 500 µl of PBS (−) containing 0.5% bovin serum albumin (referred to as "BSA" hereinbelow), for rinsing the cells. Again, the cells were subjected to centrifugation at 5,000 rpm for 30 seconds, to precipitate the cells. Thereafter, these cells were suspended in PBS (−) containing 3 µl of human serum and 16 µl of 0.5% BSA and was kept cold at 4° C. for 30 minutes. Furthermore, 2.5 µg/ml shOX40-Fc (20 µl) was added to and suspended in one of the tubes, and the resulting mixture was kept cold at 4° C. for 30 minutes, for allowing human OX40 to bind to mouse gp34. Again, 500 µl of PBS (−) containing 0.5% BSA was added to the tubes, which were then centrifuged at 5,000 rpm for 30 seconds and rinsed twice. 20 µl of fluorescein isothiocyanate (referred to as "FITC" hereinbelow)-labeled goat anti-human IgG (Fc antibody) (manufactured by CAPPEL, Co.) was added to and suspended in those tubes, which were then kept cold at 4° C. for 20 minutes. Then, the resulting suspension was suspended in 500 µl of PBS (−) containing 0.5% BSA for flow cytometer analysis with FACScan (manufactured by Becton Dickinson, Co.).

As a result, only shOX40-Fc bound to mouse gp34-expressing cell BW5147-mgp34. Based on the result, the expression of mouse gp34 on the BW5147 cell could be confirmed (FIG. 1).

The rat anti-mouse gp34 monoclonal antibody was added to and reacted with a binding reaction system for the mouse gp34-expressing cell BW5147-mgp34 and shOX40-Fc to a final concentration of 10 µg/ml. Then, flow cytometer analysis was carried out. Consequently, the fluorescence intensity of BW5147-mgp34 cell labeled via the binding of shOX40-Fc was decreased through the addition of the rat anti-mouse gp34 monoclonal antibody. The result reveals that the binding reaction of the BW5147-mgp34 cell and shOX40-Fc is inhibited by the rat anti-mouse gp34 monoclonal antibody (FIG. 2).

Example 3

Examination of Effectiveness of Rat Anti-mouse gp34 Monoclonal Antibody over Bovine Type 2 Collagen-induced Arthritis Model The effect of the rat anti-mouse gp34 monoclonal antibody over bovine type 2 collagen-induced arthritis modeling for one of autoimmune diseases, namely rheumatid arthritis in humans, was examined.

Male DBA/1J mouse (manufactured by Nippon SLC, CO.) purchased at age 7 weeks was fed under SPF conditions, to induce collagen arthritis as follows. Bovine joint-derived K42 type 2 collagen (manufactured by Collagen Technology Training Association) was dissolved in an aqueous 0.3% acetic acid solution to 4 mg/ml. An equal volume of Freund's complete adjuvant (manufactured by Wako Pure Chemical Industries, CO.) was added to the resulting solution, which was then transformed into a micell by using a sonicator. The collagen solution of 100 µl, equivalent to 200 µg collagen, was subcutaneously injected into the root of the tail of the mouse. On day 21 after the initial sensitization, furthermore, the same volume of the collagen solution was injected for booster sensitization.

Regarding the administration of the rat anti-mouse gp34 monoclonal antibody, the monoclonal antibody was intraperitoneally administered five times per week at an antibody weight ratio of 30 mg/kg·body weight for 4 weeks, after the initiation of the collagen administration for booster sensitization. To a group as a positive control for the onset of symptomatic conditions, the rat immunoglobulin G (manufactured by cappel, Co.) fraction was administered at the same weight ratio, alike. Eight animals were used for tests and controls, individually.

The arthritis symptoms were ranked according to the following 5 grades; the maximum score was 16, in total of the scores for all limbs. Scoring of arthritis symptom was carried out with the passage of time.

Score 0: no symptoms.

Score 1: only one small joint of fingers, swollen and reddened, among four limbs.

Score 2: two or more small joints or relatively large joints of hands and ankles, swollen and reddened.

Score 3: the entirety of one hand or one lower limb, swollen or reddened.

Score 4: the one hand or one lower limb at the peak of swelling and reddening.

Among the symptoms of the arthritis in the mouse, herein, the swelling and reddening of one hand or one lower limb frequently reached the peak but the swelling was gradually reduced, involving joint deformation, leading to rigid joint formation. Subsequent amelioration of the symptoms could not be followed in these cases, so the score was then ranked as 3.

As shown in FIG. 3, consequently, the onset of collagen arthritis was more greatly inhibited in the group administered with the rat anti-mouse gp34 monoclonal antibody than in the group administered with the rat immunoglobulin G.

Example 4
Examination of Effectiveness of Rat Anti-mouse gp34 Monoclonal Antibody over Experimental Autoimmune Encephalomyelitis in Mouse The effect of the rat anti-mouse gp34 monoclonal antibody over experimental autoimmune encephalomyelitis modeling for human multiple sclerosis as one of autoimmune diseases was examined.

Female SJL/J mouse (manufactured by Gokita Breeding Service, Co.) purchased at age 9 to 14 weeks was fed under SPF conditions, to induce experimental autoimmune encephalomyelitis as follows. Proteolipid protein (referred to as "PLP" hereinafter; manufactured by Sawady Technology, CO.) (200 µg) dissolved in 150 µl PBS (-) was blended with an equal weight of Freund's complete adjuvant (manufactured by Jatron, Co.), and the resulting mixture was transformed into a micell with an engaged needle, to prepare a PLP emulsified fluid. 300 µl of the emulsified fluid of 200 µg of PLP was subcutaneously administered into the flesh hummock parts of the posterior two limbs and four parts of the root of the tail, on the day of test initiation. Seven days after the initial sensitization, furthermore, the same volume of the PLP emulsified fluid was administered, for booster sensitization. During the term, 300 ng of Bordetel la pertussis toxin (manufactured by Sigma) dissolved in 200 µl PBS (-) was intraperitoneally administered on the day of test initiation and on day 2 after the test initiation. Regarding the dosing of the rat anti-mouse gp34 monoclonal antibody, the monoclonal antibody was intraperitoneally administered at a dose of 5 mg/kg·body weight every two days, 8 times, starting the initiation of the dosing of the PLP emulsified fluid for the initial sensitization, until 14 days later. To a group as positive controls for the onset of the symptomatic conditions, the same volume of rat immunoglobulin G (manufactured by Cappel, Co.) fraction was administered in the same manner to the group. Four animals were used for each of the test group and the control group.

The experimental autoimmune encephalomyelitis symptoms were ranked according to the following 6 grades; and the maximum score was 5.

Score 0: no symptoms.

Score 1: decrease of tail tension.

Score 2: mild paired paralysis impairment and motion dystonia of posterior limbs.

Score 3: severe paired paralysis impairment and motion dystonia of posterior limbs.

Score 4: paralysis of four limbs.

Score 5: death due to experimental autoimmune encephalomyelitis.

Herein, animals dead due to experimental autoimmune encephalomyelitis in each group were ranked as score 5, until the completion of the test.

The results are shown in FIG. 4. The scores of the grades in each group are shown on average. The onset of the symptomatic conditions of experimental autoimmune encephalomyelitis was more highly suppressed in the group dosed with the rat anti-mouse gp34 monoclonal antibody than in the group dosed with the rat immunoglobulin G.

ADVANTAGES OF THE INVENTION

In accordance with the invention, it is indicated that the rat anti-mouse gp34 monoclonal antibody binding to mouse gp34 thereby inhibiting the binding of mouse gp 34 to mouse OX40 inhibits the onset of bovine type 2 collagen arthritis as a model of rheumatoid disease and the onset of experimental autoimmune encephalomyelitis as a model of multiple sclerosis. When the humanized anti-human gp34 monoclonal antibody is used to inhibit the cellular signal transduction between antigens gp34 and OX40 via the membrane-binding type proteins of both the antigens, inclusive of at least currently known immune cells, the effect thereof over the prophylaxis and therapeutic treatment of autoimmune diseases including multiple sclerosis including rheumatoid arthritis, sarcoidosis, autoimmune uveitis and inflammatory bowel disease, and graft-versus-host disease, can be exerted. Based on such characteristic properties, a pharmaceutical composition containing the humanized anti-human gp34 monoclonal antibody provided in accordance with the invention is promising as a useful pharmaceutical agent of human autoimmune diseases.

Reference to the deposited microorganism under Rule No.13-2 1. TOL-1 a. Name and Address of the depository organization to which the microorganism has been deposited Name: National Institute of Bioscience and Human-Technology, Agency of Industrial Science and Technology, Ministry of International Trade and Industry Address: 1-3, Higashi 1 chome, Tsukuba-shi, Ibaraki-ken, Japan-(〒305-8566)

b. Date of deposition at the depository organization described in a.

Sep. 18, 1998 c. Accession No. designated on the deposition by the depository organization

FERM BP-6509

What is claimed is:

1. A method of treating rheumatoid arthritis comprising administering a monoclonal antibody against a human T-cell leukemia virus-derived transcription activating factor p40Tax-induced cell membrane glycoprotein of 34 kDa (gp34) in an amount effective for treating rheumatoid arthritis to a patient in need of such treatment, wherein said monoclonal antibody inhibits the binding of said human gp34 to human OX40.

2. A method of treating multiple sclerosis comprising administering a monoclonal antibody against a human T-cell leukemia virus-derived transcription activating factor p40 Tax-induced cell membrane glycoprotein of 34 kDa (gp34) in an amount effective for treating multiple sclerosis to a patient in need of such treatment, wherein said monoclonal antibody inhibits the binding of said human gp34 to human OX40.

* * * * *

Adverse Decision In Interference

Patent No. 6,333,035, Kazuo Sugamura, Kazuko Murata, Norikazu Higashimura, MEDICINAL COMPOSITION CONTAINING GP34 BINDING-INHIBITOR AS THE ACTIVE INGREDIENT, Interference No. 105,275, final judgment adverse to the patentees rendered, September 29, 2005, as to claims 1, 2.

*(Official Gazette, February 28, 2006)*